(12) United States Patent
Kouge et al.

(10) Patent No.: US 7,977,379 B2
(45) Date of Patent: Jul. 12, 2011

(54) METHOD FOR ANGIOGENESIS INHIBITION OR IMMUNOSTIMULATION

(75) Inventors: Takashi Kouge, Kurashiki (JP); Akihiro Yamashita, Bizen (JP); Keno Ishihara, Tokyo (JP)

(73) Assignee: BHN Co., Ltd., Tokyo (JP)

( * ) Notice: Subject to any disclaimer, the term of this patent is extended or adjusted under 35 U.S.C. 154(b) by 256 days.

(21) Appl. No.: 10/439,020

(22) Filed: May 15, 2003

(65) Prior Publication Data

US 2004/0029955 A1 Feb. 12, 2004

(30) Foreign Application Priority Data

May 15, 2002 (JP) ................. 2002-177774
Apr. 7, 2003 (JP) ................. 2003-136601
May 9, 2003 (JP) ................. 2003-131997

(51) Int. Cl.
*A61K 31/32* (2006.01)
*A61K 31/19* (2006.01)

(52) U.S. Cl. .................. 514/459; 514/566
(58) Field of Classification Search .............. 514/424, 514/177, 178, 171, 182, 56, 459, 566
See application file for complete search history.

(56) References Cited

U.S. PATENT DOCUMENTS

| | | | | |
|---|---|---|---|---|
| 4,975,422 | A * | 12/1990 | Kanoh et al. | 514/8 |
| 4,986,982 | A * | 1/1991 | Scott | 424/63 |
| 4,994,443 | A | 2/1991 | Folkman et al. | |
| 5,001,116 | A | 3/1991 | Folkman et al. | |
| 6,221,910 | B1 * | 4/2001 | Montner | 514/563 |
| 6,391,332 | B1 * | 5/2002 | Somerville et al. | 424/439 |
| 6,407,066 | B1 * | 6/2002 | Dressen et al. | 514/19 |
| 6,465,218 | B1 | 10/2002 | Horiuchi et al. | |
| 6,977,311 | B2 * | 12/2005 | Kochat et al. | 562/571 |
| 2002/0169202 | A1 | 11/2002 | Sakamoto et al. | |
| 2003/0064484 | A1 | 4/2003 | Horiuchi et al. | |
| 2003/0068329 | A1 | 4/2003 | Kosuna et al. | |
| 2004/0248967 | A1 | 12/2004 | Sakamoto et al. | |
| 2009/0004247 | A1 | 1/2009 | Kosuna et al. | |

FOREIGN PATENT DOCUMENTS

| | | |
|---|---|---|
| GB | 2 341 800 | 3/2000 |
| JP | 58131978 | 8/1983 |
| JP | H6-62413 | 3/1987 |
| JP | 63-119500 | 5/1988 |
| JP | 10-147534 | 6/1988 |
| JP | 6-62426 | 4/1991 |
| JP | 08-2666246 | 10/1996 |
| JP | 10-287584 | 10/1998 |
| JP | 10-298099 | 11/1999 |
| JP | 2000-159682 | 6/2000 |
| JP | 3071068 | 7/2000 |
| JP | 3120187 | 12/2000 |
| JP | 2001-240603 | 9/2001 |
| JP | 2001-269163 | 10/2001 |
| JP | 2001-333731 | 12/2001 |
| JP | 2002-065206 | 3/2002 |
| JP | 2002-220335 | 8/2002 |
| JP | 2004-018483 | 1/2004 |
| WO | WO 01/44488 | 6/2001 |

OTHER PUBLICATIONS

Kim et al. Bioresource Tecnology 89 (2003) 81-87.*
Grever et al., Seminars in Oncology, 19(6), 1992, pp. 622-638, especially pp. 626-627).*
www.musclemaster.net/beverly-mass-amino.html (Mar. 2003).*
Kahner et al. Phytochemistry, 49(6) 1693-1697, 1998.*
Ann Rheum Dis 2001;60:iii71-iii74.*
kahlon et al. Can J Cardiol. Jan.-Feb. 1992;8(1):60-4.*
Takaku et al. J. Nutrition 131:1409-1413, 2001.*
Life Extension Magazine (1999) 1-9.*
Dunitz et al. (1995) Acta Cryst C51: 1377 1379.*
Toth et al. Cancer research, 1978 V38 (1) p. 177-80.*
U.S. Department of Health and Human Services, U.S. Food and Drug aAdministration, FDA Backgrounder, Aug. 31, 1995.*
Hagenbart S. L. Food Product Design: Applications-Alternative Enhancers found at www.foodproductdesign.com, Feb. 1998.*
Yoshiaki et al Nippon Shokuhin Kagaku Kaishi vol. 45(4) 246-252, 1998.*
Twardzik et al Proc. Nat. Acad. Sci. USA vol. 69(1) p. 274 (abstract), 1972.*
Answers.com (definition of prevention), 2005.*
Zest for life-www.anyvitamins.com (1999-2003).*
Maity et al (1999) Pathology Oncology Research V5(4)309-314.*
Ng T.B. A review of research on protein-bound polysaccharide (polysaccharopeptide PSP) from the mushroom *Coriolus versicolor* (basidiomycetes: polyporaceae) Gen. Pharm. vol. 30 (1) p. 1-4 (1998).*
Younan A, Sidky et al, Cancer Research, 47, p. 5155-5161, Oct. 1, 1987.
Shuichi Mizuno et al., Wakan Iyakugaku Zasshi, 15, p. 334-335.
Yoshiaki Fujimiya et al, Nippon Shokuhin Kagaku Kogaku Kaishi, vol. 45, No. 4, p. 246-252, Apr. 1998.
J. Kollonitsch et al, Chemistry and Industry, No. 7, p. 1867, Nov. 7, 1964.
Antonino Passaniti et al, Laboratory Investigation, vol. 67, No. 4, p. 519-528, 1992.
Antonio Passaniti, et al., Methods in Laboratory Investigation, A Simple, Quantitative Method for Assessing Angiogenesis and Antiangiogenic Agents Using Reconstituted Basement Membrane, Heparin, and Fibroblast Growth Factor, Laboratory Investigation, vol. 67, No. 4, p. 519, 1992.
Notice of Reasons for Rejection for patent application No. 2003-131997 Dispatch No. 118514, Dispatch Date: Feb. 23, 2010.
Patent Abstracts of Japan, JP 2002-065206, May 2002.
Patent Abstracts of Japan, JP 2000-159682, Mar. 2000.
Patent Abstracts of Japan, JP 2001-269163, Feb. 2001.

(Continued)

*Primary Examiner* — Brandon J Fetterolf
*Assistant Examiner* — Shirley V Gembeh
(74) *Attorney, Agent, or Firm* — James B. Conte; Husch Blackwell LLP

(57) ABSTRACT

The present invention relates to a composition for use in prevention or treatment of a vascular-related disease, particularly used for angiogenesis inhibition, tumor growth inhibition or tumor metastasis inhibition, or immunostimulation, which comprises glutamic acid or derivatives thereof, preferably glutamic acid is anhydrous glutamic acid represented by Formula (1) or pyroglutamic acid, and a pharmaceutically acceptable carrier or an edible carrier, and a method of preventing or treating a vascular-related disease.

2 Claims, No Drawings

OTHER PUBLICATIONS

Patent Abstracts of Japan, JP 10-298099, Nov. 1998.
Patent Abstracts of Japan, JP 2001-333731, Dec. 2001.
Patent Abstracts of Japan, JP 2001-240603, Sep. 2001.
Patent Abstracts of Japan, JP 08-266246, Oct. 1996.
Patent Abstracts of Japan, JP 10-287584, Oct. 1998.
Dispatch No. 761478, Dispatch Date—Nov. 17, 2009 "Notice of Reasons for Rejection" with English translation for Parent Patent Application No. 2003-13601 (6 pages).
Machine translation for JP 2002-220335 (abstract only), Aug. 2002.
Machine translation for JP 2004-018483, Jan. 2004.
Search Report from Companion Taiwanese case Application No. 092113214 (1 page).
Office Action issued in companion Taiwanese case Application No. 092113214 with English translation (8 pages).

* cited by examiner

METHOD FOR ANGIOGENESIS INHIBITION OR IMMUNOSTIMULATION

The present application is based on Japanese Patent Application No. 2002-177774, Japanese Patent Application filed Apr. 7, 2003, and Japanese Patent Application No. 2003-131997, the entire contents of which are incorporated herein by reference.

BACKGROUND OF THE INVENTION

1. Field of the Invention

The present invention relates to a method for angiogenesis inhibition, neoplasm depression or immunostimulation. etc. which comprises administering to a person or an animal anhydrous glutamic acid, pyroglutamic acid, or derivative thereof as active ingredient.

2. Prior Art

A vascular-related disease includes, for example, propagation and transition of neoplasm, inflammation, rheumatoid arthritis, diabetic retinopathy, and psoriasis, and it is greatly related with angiogenesis and immune function. Angiogenesis is phenomenon of generating new capillary blood vessels in animal tissues or organs, in the process of which, vascular basement membrane is disassembled and attacked by protease, vascular endothelial cell is grown by migration and bonded to extra cellular matrix, vascular endothelial cell is differentiated, and vascular cavity is formed. In general, new blood vessels are formed and extended in childhood and growth period. However, when growth period is past, the occasion of angiogenesis in the body is limited. Angiogenesis is observed under normal physiology condition such as luteinization, ovulation, embryogenesis, and placentation, and also occurred in cure process of lesion and resealing process of inflammation. As described above, angiogenesis occurs in normal state and has an important role in restoration of tissues, but it is known that capillary increases in a lot of chronic diseases such as diabetes mellitus and that angiogenesis causes grave lesion to tissues.

Angiogenesis is involved in etiology and aggravation of case of various diseases. The diseases include enhancement and transition of malignant, diabetic retinopathy, neovascular glaucoma, inflammatory dermatosis, joint fluid rheumatism, osteoarthritis, atherosclerosis, and obstructive affection such as myocardial infarction.

For example, when malignant tumor multiplies, tumor cell induces vascular neogenesis for itself by angiogenesis promoter to get nourishment and oxygen which are necessary for propagation of tumor cell, and tumor cell further grows while getting nutrient through new blood vessels. Transition of tumor cell to other organ and site also induces angiogenesis, and tumor cell is carried by the bloodstream. In the case of diabetic retinopathy, capillary is clogged up because of the viscosity blood set up by diabetes mellitus and is affected, and bleeding and edema are produced in retina. When bleeding and edema are chronic, the retina falls short of oxygen and nourishment, and then newborn blood vessel originates on the retina or nervous system mammilla so that fiber tissue is formed circumferentially. The retina is pulled by means of the fiber tissue (retinal detachment) or the retinal blood vessel is occurred bleeding (vitreous hemorrhage), and then serious visual handicap or blindness is occurred before long.

As described above, because angiogenesis is deeply involved in the onset and development of various diseases, a lot of searches of materials inhibiting angiogenesis have been done hitherto and investigation is pushed forward at the present zealously as an aim in a treatment or prevention of these diseases. As material and drug with action inhibiting angiogenesis, sulfation polysaccharide (Japanese Patent Laid-Open No. S63-119500 bulletin), trafermin, heparin and steroid (U.S. Pat. No. 4,994,443 specification; or U.S. Pat. No. 5,001,116 specification), ascorbic acid ether and this related-compound (Japanese Patent Laid-Open No. S58-131978 bulletin), interferon alpha or interferon beta (Sidky et al., "Cancer Research", 47:5155-5161, (1987)), thiazole derivative (Japanese Patent Publication No. H6-62413 bulletin), shark cartilage extract (chondroitin and mucopolysaccharide) (Japanese Patent Laid-Open No. H10-147534 bulletin), polysaccharide derived from streptococcus bacteria (Japanese Patent Publication No. H6-62426 bulletin), O-displacement fumagillol derivative (Japanese Patent No. 3120187 bulletin), neo agarose oligosaccharide (Japanese Patent No. 3071068th bulletin) etc. are proposed.

However, considering practical side, all of the materials having action of angiogenesis inhibition proposed or examined till now as a material did not show the sufficiently satisfied effect. The materials were used based on experimental findings under the dosage condition that is not practical, the materials had worries about adverse reactions, or the materials must be administered in high doses in use. Therefore, the development of materials by which angiogenesis is inhibited more effectively and materials to be used without any worry in a point of safety is demanded.

SUMMARY OF THE INVENTION

Accordingly, it is an object of the invention to provide a method for angiogenesis inhibition that inhibits angiogenesis strongly, method for neoplasin inhibition, or method for immunostimulation.

According to the feature of the invention, a method for 'angiogenesis inhibition' or 'immunostimulation' comprises administering to a person or an animal anhydrous glutamic acid represented by Formula (1), pyroglutamic acid represented by Formula (2), or a salt or amide thereof and a pharmaceutically acceptable carrier or an edible carrier.

(1)

(2)

In accordance with a preferred embodiment of the invention, the anhydrous glutamic acid and pyroglutamic acid are L-type or DL-type. The anhydrous glutamic acid, pyroglutamic acid and said salt or amide thereof are used in form of fruit body of Basidiomycetes or mycelium, a dry powder thereof, or an extract or a purified material thereof. Preferably, the Basidiomycetes is one or more kinds selected from the group consisting of *Lentinus edodes, Flammulina velutipes, Lyophyllum aggregatum, Pleurotus ostreatus, Agaricus* fungus, *Phellinus linteus* fungus, *Ganoderma lucidum, Hericium Erinaceum* fungus, *Coriolus versicolor, Agaricus campestris, Grifola frondosa, Sparassis erispa, Schizophyllum commune, Tremella fuciformis* Berkeley, and *Cordyceps sinensis* (tochukaso).

The extract is extracted by using "water and/or a hydrophilic organic solvent", or "water and/or a hydrophilic organic solvent and a hydrophobic organic solvent". The hydrophilic organic solvent is methanol, ethanol, acetone or propanol, and the hydrophobic organic solvent is hexane or chloroform. The method is used for tumor growth inhibition or tumor metastasis inhibition.

DETAILED DESCRIPTION OF THE PREFERRED EMBODIMENTS

A method of the present invention will be explained in detail in the following.

In an anhydrous glutamic acid or derivatives thereof contained as essential component in a method of the present invention, anhydrous glutamic acid have the structure that glutamic acid is intramolecular-dehydrated and become circular as shown in above-mentioned structural formula.

Similarly, in pyroglutamic acid (2-pyrrolidone-5-carbonxylic acid) or derivatives thereof contained as essential component in a method of the present invention, pyroglutamic acid also have the structure that glutamic acid is intramolecular-dehydrated and become circular.

Both anhydrous glutamic acid and pyroglutamic acid concerning the present invention can be got by means of chemical synthesis, enzymatic method, or hydrolysis process, extraction process or the like from natural product. In all of these methods, L-glutamic acid, D-glutamic acid or DL-glutamic acid of optical isomer can be used as glutamic acid, but L-glutamic acid or DL-glutamic acid is preferable in view of effect of the invention, and, besides, L-glutamic acid is the most desirable.

The derivative anhydrous glutamic acid is hydrochloride salt of anhydrous glutamic acid. The derivative of pyroglutamic acid is sodium salt of an anhydrous glutamic acid.

Anhydrous glutamic acid can be synthesized in accordance with well known method (for example, J. Kollonitsch and A. Rosegay, Chemistry and Industry, 7: 1867, (1964)). For instance, thionyl chloride is added in trifluoroacetic acid solution including L-glutamic acid, and dehydration reaction is caused, and diethyl ether is added there to produce sediment, and then under refrigeration anhydrous L-glutamic acid can be prepared by recrystallization using diethyl ether. In addition, various derivatives can be synthesized chemically or enzymatically by conventional method using this anhydrous L-glutamic acid as starting material.

Pyroglutamic acid and derivatives thereof can be synthesized chemically in accordance with well known method, for example, L-glutamic acid and water (equal weight each other) is heat-treated at about 130-150 degrees Celsius in autoclave to prepare L-pyroglutamic acid, or heat-treated at about 190-200 degrees Celsius to prepare DL-pyroglutamic acid by racemization. In addition, various derivative can be synthesized chemically or enzymatically by conventional method using this L-pyroglutamic acid or DL-pyroglutamic acid as starting material.

The following method can be used to prepare anhydrous glutamic acid of the present invention from natural product. Protein or peptide derived from animals, plants, fish and shellfish are hydrolyzed by hydrochloric acid or protease etc. and further refined to prepare anhydrous glutamic acid. Fruit body of Basidiomycetes or mycelium is used preferably as raw materials. These are dried to give powder thing, or extract-processed using extracting solvent to give extract solution or concentrated solution, which are dried to give extract, and further separated or fractionated using organic solvent or adsorbent to prepare purified material of high concentration.

In the present invention, these are used as preferred embodiment of anhydrous glutamic acid and derivatives thereof.

When pyroglutamic acid is prepared from natural product, purified material of high concentration can be prepare by the method same as anhydrous glutamic acid, these are used as preferred embodiment of pyroglutamic acid and derivatives thereof.

In here, it is preferable to use one or more materials selected from group comprising of *Lentinus edodes, Flammulina velutipes, Lyophyllum aggregatum, Pleurotus ostreatus*, Agaricus fungus, *Phellinus linteus* fungus, *Ganoderma lucidum, Hericium Erinaceum* fungus, *Coriolus versicolor, Agaricus campestris, Grifola frondosa, Sparassis crispa, Schizophyllum commune, Tremella fuciformis* Berkeley, and *Cordyceps sinensis* (tochukaso) as Basidiomycetes. All of these fruit bodies of mushroom are cultivated artificially or harvested abundantly, and are in the marketplace, therefore there are available easily. These are eaten raw, or as dried material, the powder, or extract etc . . . . In addition, there are materials that polysaccharides included in extract like *Lentinus edodes, Coriolus versicolor,* or *Schizophyllum commune* are used as drug. In the present invention, judging from desired effect, one kind or more kinds chosen among group comprising of Agaricus mushroom, *Phellinus linteus, Ganoderma lucidum, Hericium Erinaceum* fungus and *Cordyceps sinensis* (tochukaso) are more preferable, and Agaricus fungus is the most desirable.

*Agaricus* mushroom is fungus of Agaricaceae and belongs to *Agaricus* genus, and *Agaricus blazei* Murill or *Agaricus bisporus* can be illustrated. It is known that the former includes polysaccharide (beta-D-glucan) and polysaccharide protein conjugate and have antitumor action and hypoglycemic action. *Phellinus linteus* is fungus of Hymenochaetaceae, and it is said that polysaccharide of the hot water-extract shows anticancer action. *Ganoderma lucidum* is fungus of Polyporaceae s. l. and also referred to as *Ganoderma lucidum*. Antiallergic action, antitumor action, and blood pressure stabilization action by terpenoid and polysaccharide, and hypoglycemic action etc. by proteoglycan are known. A *Hericium erinaceum* mushroom belongs to *Hericium ramosum* (Merat) Banker, and then anticancer action by heterozygous beta-D-glucan component and active oxygen-erasing action are known.

In the present invention, plain or dried fruit body of the Basidiomycetes can be used as raw materials. However, dried fruit body is preferable in view of handling, keeping quality and extraction efficiency. Plain or dried mycelium, which is prepared by incubation of inoculm using culture medium including suitable carbon source and nitrogen source, can be used. And then, dried mycelium is convenient same as case of the fruit body.

In addition, according to the present invention, mycelium can be used as raw materials, and culture broth generating in mycelium production can be also used.

The culture broth is concentrated appropriately, and purified using solvents as described in the following.

In the present invention, it is characterized that anhydrous glutamic acid and derivatives thereof and pyroglutamic acid and derivatives thereof of the present invention are extracted by "water and/or hydrophilic organic solvent", or "water and/or hydrophilic organic solvent and hydrophobic organic solvent" from fruit body of the Basidiomycetes or mycelium. Desired effect of the present invention does not almost appear in extract that is extracted by only hydrophobic organic solvent. Methanol, ethanol, n-propanol, isopropanol or acetone is desirable for hydrophilic organic solvent, and hexane or chloroform is desirable for hydrophobic organic solvent. Hydrophilic organic solvent can be used in mixture with water, and each of hydrophilic organic solvent and hydrophobic organic solvent can be used in single or mix. The important thing on extraction of active ingredient of composition of the present invention is following point. More specifically, extract including water-soluble component mainly is given by using "water and/or hydrophilic organic solvent", or mix solvent with hydrophobic organic solvent, and readily-soluble component such as saccharide or amino acid, which is more water-soluble, is separated and removed by using hydrophilic organic solvent, and then oiliness component such as lipid class is separated and removed by using hydrophobic organic solvent.

When hydrophilic organic solvent and hydrophobic organic solvent are mixed, preferable mix ratio (volume ratio) is former/latter=9/1-1/9, more preferably, 5/1-1/5, and most preferably, 3/1-1/1. Extraction efficiency of essential component of the present invention deteriorates possibility and desired Effect is not provided possibility when mix ratio gets out of the range. Extracting solvent is used in weight of about 3-20 times against dried material or extract of fruit body or mycelium. When it is less than 3 times, yield of extract is low. On the contrary, if using a large quantity beyond 20 times, extraction efficiency does not improve more.

Extract solution is given by extraction process which is carried out, while fruit body of Basidiomycetes or mycelium come in contact with the extract solvent, for about 10 minutes to about 10 hours under normal pressure or pressurized, preferably 1 to 3 air pressure, at room temperature or around 100 degrees Celsius while stirring or reflowing appropriately. The solvent of the extract solution is removed by vacuum-dry, freeze-dry, or spray-dry etc. to prepare extract of Basidiomycetes. In addition, the extract is fractionated by hydrophilic organic solvent and hydrophobic organic solvent to give concentrate which is further raised content of essential component of the present invention. Furthermore, the concentrate is run through column chromatography with adsorbent such as silica gel, activated alumina, magnesium silicate, activated carbon, cellulose, or ion exchange resin to fractionate, and then purified material of high concentration can be prepared.

As above described, anhydrous glutamic acid, pyroglutamic acid, or derivatives thereof prepared by chemical synthesis or extract-method from Basidiomycetes, and the extract solution, extract, concentrate, or purified material including thereof, can be used for making composition for angiogenesis inhibition of the present invention with or without appropriate carrier, excipient, or additive. As far as, in composition for angiogenesis inhibition of the present invention, it is not against a purpose of the present invention, various kinds of raw materials and component are used together, for example, excipient, desiccant, antiseptic, nutrient, thickener, emulsifier, antioxidant, sweetener, acidulant, flavor enhancer, colorant, or flavor, which is used for conventional food and drug, as pharmaceutically acceptable carrier or edible carrier. In addition, it is one of the preferable aspects of the present invention to use well-known material having action inhibiting angiogenesis together.

In addition, composition of the present invention is also the thing which functions as composition for use in neoplasm inhibition or immunostimulation, and prominent effect is shown. In other words, composition of the present invention acts as composition for use in prevention or treatment of a vascular-related disease, and shows, besides angiogenesis inhibitory action, antitumor action, namely inhibition action of development and metastasis of tumors, and further immunoenhancement action by oral ingestion etc . . . . In addition, there is effect for rheumatoid arthritis, diabetic retinopathy, psoriasis, neovascular glaucoma, inflammatory dermatosis, joint fluid rheumatism, osteoarthritis, atherosclerosis, obstructive affection such as myocardial infarction. Therefore, the composition can be utilized as composition having above actions, and eating or drinking product, drug, pet food, or fodder for domestic livestock or domestic chickens etc. can be illustrated for a concrete embodiment of the composition. Especially, eating and drinking product and drug are desirable.

As an embodiment of eating and drinking product, dry powder, extract, or purified material of the Basidiomycetes, or the composition including them can be added in liquid, gel, powder, or solid food. For example, these can be added in fruit beverage, refreshing drinks, tea, soup, jelly, yogurt, pudding, cake mixture, furikake (powdered food to be sprinkled over rice), miso (bean paste), soy sauce, dressing, mayonnaise, flavor enhancer such as dip of grilled beef, noodles, processed food of meat and fish such as ham or sausage, jam, cow milk, cream, powder, solid, or liquid milk-product such as butter or cheese, margarine, bread, cake, or cookie etc . . . .

In addition, these are processed into powder, granule, pellet, tablet along with dextrin, lactose, starch or elaboration material thereof, excipient such as cellulose, vitamin, mineral, fat and oil of flora and fauna and fish and shellfish, protein, sugar, coloring agent, flavor, other above edible additive, if necessary, and these are covered in gelatine, and these are molded as capsule, and these are made to health drink usable as nutritional supplementary food and health food. Then, the composition that used well-known edible material having angiogenesis inhibition action together is preferred. In addition, eating and drinking product of the present invention extends over extremely various kinds of forms, it is not limited to these illustrations, but above forms of the nutritional supplementary food and health food are desirable.

In the present invention, compounding dosage of composition of the present invention in eating and drinking product is hard to be prescribed uniformity because of differences in kind, form, or use purpose of the eating and drinking product, and kind or form of composition to combine, but when adding in general processed food, about 0.01-50% by weight, more preferably 0.1-30% by weight on the basis of anhydrous glutamic acid or pyroglutamic acid. When dosage gets out of the range and is under 0.01%, desired effect of the present invention by oral ingestion is small. On the contrary, if dosage is too much, a flavor is harmed potentially by kind of eating and drinking product, and there is the case that it becomes impossible to prepare the eating and drinking product.

In embodiments as drug of the present invention, above composition is added well-known excipient or additive which is not against a purpose of the present invention, if necessary, and it was processed by conventional method to form preparation such as tablet, capsules, granulation, powder, or injection. By oral administration, enteral administration, blood vessel administration, or intradermal injection, the composition can be used to develop at least one of effect of angiogenesis inhibition, tumor inhibition, or immunostimulation, and the composition can be applied to prevent or treat various diseases accompanied by vascular neogenesis, propagation and transition of tumor, or reduction of immunocompetence. Combination dosage of composition of the present invention is hard to be prescribed uniformity because of differences in kind, form, or use purpose of the preparation for medicine, but about 0.01-70% by weight, on the basis of anhydrous glutamic acid or pyroglutamic acid. In case of oral administration, dosage is not limited in particular, but it is 0.01-20 g, more preferably 0.1-10 g as base in anhydrous glutamic acid or pyroglutamic acid per adult (50 kg in weight)/1 day. When dosage gets out of the range and is under 0.01 g, desired effect of the present invention is small. On the contrary, if dose is too much, prominent effect cannot be expected more.

Example 1

Dry fruit body of an agaricus mushroom (*Agaricus blazei* Murill) was crushed. It was then added with chloroform/methanol=1/1 mixed solution after which the mixture was warmed to 40 degrees Celsius, and extract-processed for one hour to give a chloroform/methanol=1/1 extract. Methanol was added to the extract, and methanol soluble layer was separated and collected. Furthermore, hexane was added in the methanol soluble layer, and hexane insoluble layer (sample 1) was collected. The hexane insoluble layer was then run through a silica gel column chromatography (silanised Silicagel 60 PF 256: Merck 7751, water/methanol=7/3), and ninhydrin reaction positive fractions (fraction No. 5 and 6) were collected. The fractions (fraction No. 5 and 6) were then run through HPLC (ShimpakPREP-ODS (M), column: 20φ×250 mm, Shimadzu, RT, 6 ml/min, water/methanol=5/1), and ninhydrin reaction positive fractions (Rt=6 to 12 min) were collected. The fractions (Rt=6 to 12 min) were further run through HPLC (ShimpakPREP-ODS (M), column: 20φ×250 mm, Shimadzu, RT, 6 ml/min, water), and ninhydrin reaction positive fraction (Rt=8 to 22 min) were collected. These ninhydrin reaction positive fractions were further refined by running through TLC (Silicagel 60 PF 254:Merck7747, water/methanol=1/100), and it was ensured that an anhydrous glutamic acid was included (Rf=0.41). In addition, results of mass spectrum and nuclear magnetic resonance (NMR) analysis showed that the anhydrous glutamic acid was L-optical isomer.

Example 2

By means of culture apparatus "JARFERMENTER" of 10 liters capacity, while aerating (2 vvm), inoculum culture broth of *Phellinus linteus* (1 liter) was incubated in culture medium including glucose (5% by weight), yeast extract (0.5% by weight) and peptone (2.0% by weight) at 28 degrees Celsius for 72 hours, and culture mycelium (165 g) was collected. The mycelium was dried and crushed to give mycelium powder. A hexane/ethanol/water=2/3/1 mixed solvent was then added to the mycelium powder after which the mixture was extract-processed at room temperature for three hours to give an extract (sample 2). The extract was further fractionation-processed by ethanol, and an ethanol soluble layer was separated and collected. The ethanol soluble layer was then fractionation-processed by hexane, and hexane insoluble layer was collected. The hexane insoluble layer was fractionated and purified by silica gel column chromatography, HPLC, and TLC as same as example 1. Existence of anhydrous L-glutamic acid was ensured from results of mass spectrometry and nuclear magnetic resonance assay.

Example 3

In accordance with a method as described in the above documents, an anhydrous L-glutamate was synthesized. More specifically, trifluoroacetic acid 75 ml and L-glutamic acid mol were added to four-mouth flask, and the mixture was stirred to dissolve. While stirring the solution, thionyl chloride 0.28 mol was dripped slowly into the flask. 30 minutes later of end of dripping, diethyl ether 35 ml were added slowly into the flask to produce sediment. After holding to 5 degrees Celsius for one hour, diethyl ether 100 ml were added to repeat recrystallization. An anhydrous L-glutamate acid hydrochloride (sample 3) was then prepared.

Example 4

An anhydrous DL-glutamate acid hydrochloride (sample 4) was prepared using the same way as in example 3 except that DL-glutamic acid substituted for L-glutamic acid of raw materials.

Example 5

Dry fruit body of *Agaricus blazei* Murill was crushed, and water was added there to extract-process using hot water at 80-95 degrees Celsius by conventional method. The extract was then dried under reduced pressure to prepare a hot water-extract of agaricus fungus. Ethanol multiplied by three (weight) was added to 40% by weight aqueous solution of the hot water-extract, and after mixing, ethanol layer was collected. The ethanol layer was then dried under reduced pressure to prepare ethanol soluble material (sample 5).

Comparative Example 1

Dry fruit body of *Agaricus blazei* Murill, and water was added to extract-process using hot water at 80-95 degrees Celsius by conventional method. The extract was then dried under reduced pressure to prepare a hot water-extract of agaricus fungus corresponding to marketing product (reference sample 1).

Test Example 1

Angiogenesis inhibition action of anhydrous glutamic acid, its derivatives, and various processed materials containing them concerning the present invention was examined by degree of angiogenesis induced by means of MATRIGEL™ matrix (made by Becton Dikinson Labware Company, it is "cell culture backing material", following "MATRIGEL".) according to a method of Passaniti et al (Laboratory Invest., Vol. 67, Page 519-528, 1992).

An example of the MATRIGEL matrix is shown with the following: BD Matrigel Basement Membrane Matrix is a solubilized basement membrane preparation extracted from the Engelbreth-Holm-Swarm (EHS) mouse sarcoma, a tumor rich in ECM proteins. Its major component is laminin, followed by collagen IV, heparan sulfate proteoglycans, entactin and nidogen.35 It also contains TGF-β fibroblast growth factor, tissue plasminogen activator36 and other growth factors which occur naturally in the EHS tumor. At room temperature, BD Matrigel Matrix polymerizes to produce biologically active matrix material resembling the mammalian cellular basement membrane.

More specifically, normal mice (5 mice/1 group) were used after breeding C57BL/6 female mice (5 week old, purchased from Charles River JAPAN, Inc.) preliminarily for one week. While cooling test materials as shown in the following, each of the test materials 0.5 ml were transplanted to subcutaneous of abdomen of the mice. MATRIGEL was taken out on the sixth day after transplantation, and state of angiogenesis was observed. In addition, the MATRIGEL was freeze-dried, and it was estimated the weight. Furthermore, pure water 1 ml was added to the MATRIGEL. After homogenizing by Polytron and centrifuging at 2000 rpm for five minutes, supernatant was filtrated through filter with 0.2 μm and hemoglobin dosage was measured by using Hemoglobin-TestWako™ (made by Wako Pure Chemical Industries, Ltd.).

Group 0 of nothing addition: MATRIGEL

Control group: MATRIGEL, heparin (64 units), Acidic Fibroblast Growth Factor (it is abbreviated to a-FGF as follows.) (1 ng/ml)

Group 1 of test material addition: MATRIGEL, heparin (64 units), a-FGF (1 ng/ml), sample 3 (800 μg/ml)

Group 2 of test material addition: MATRIGEL, heparin (64 units), a-FGF (1 ng/ml), sample 3 (400 μg/ml)

Group 3 of test material addition: MATRIGEL, heparin (64 units), a-FGF (1 ng/ml), sample 3 (200 μg/ml)

Group 4 of test material addition: MATRIGEL, heparin (64 units), a-FGF (1 ng/ml), sample 4 (800 μg/ml)

Group 5 of test material addition: MATRIGEL, heparin (64 units), a-FGF (1 ng/ml), sample 1 (600 μg/ml)

Group 6 of test material addition: MATRIGEL, heparin (64 units), a-FGF (1 ng/ml), sample 2 (800 μg/ml)

Group 7 of test material addition: MATRIGEL, heparin (64 units), a-FGF (1 ng/ml), sample1+sample 3 (for each 200 μg/ml)

Group 8 of test material addition: MATRIGEL, heparin (64 units), a-FGF (1 ng/ml), sample 5 (600 μg/ml)

Group 9 of test material addition: MATRIGEL, heparin (64 units), a-FGF (1 ng/ml), reference sample 1 (800 μg/ml)

A result of the test was shown in Table 1 and Table 2. The numerical values of each table were displayed in n=5, average value±standard error. As is apparent from each table, in control group, angiogenesis was promoted remarkably and weight of MATRIGEL and hemoglobin dosage were increased compared with a group 0 of nothing addition. On the other hand, in groups of test material addition, augmentation of weight of MATRIGEL and hemoglobin dosage were concentration-dependent controlled at the group using sample 3 (anhydrous L-glutamate acid hydrochloride), and these results showed excellent angiogenesis inhibition effect. The group using sample 4 (anhydrous DL-glutamate acid hydrochloride) was also recognized an effect, which is slightly low, but almost equal to sample 3, of angiogenesis inhibition. In addition, sample 1 (purification material of agaricus mushroom extract) and sample 2 (extract of *Phellinus linteus*) also showed strong angiogenesis inhibition effect. However, the angiogenesis inhibition effect was small with reference sample 1 (hot water extract of an agaricus mushroom).

TABLE 1

| No. | Group | material (μg/mL) | MATRIGEL Matrix weight (mg) n = 5 |
|---|---|---|---|
| 1 | Group 0 (Normal) | | 77.7 ± 10.1 |
| 2 | Control | | 413.3 ± 42.5 |
| 3 | Group 1 | sample 3 (800) | 110.9 ± 11.4 |
| 4 | Group 2 | sample 3 (400) | 232.2 ± 52.7 |
| 5 | Group 3 | sample 3 (200) | 276.6 ± 27.6 |
| 6 | Group 4 | sample 4 (800) | 237.3 ± 30.1 |
| 7 | Group 5 | sample 1 (600) | 105.0 ± 12.3 |
| 8 | Group 6 | sample 2 (800) | 149.4 ± 24.7 |
| 9 | Group 7 | sample 1/sample 3 = 1/1 (400) | 167.3 ± 33.2 |
| 10 | Group 8 | sample 5 (600) | 181.1 ± 20.2 |
| 11 | Group 9 | reference sample 1 (800) | 357.5 ± 36.2 |

TABLE 2

| No. | Group | material (μg/mL) | Quantity of hemoglobin (mg) n = 5 |
|---|---|---|---|
| 1 | Group 0 (Normal) | | 4.6 ± 1.0 |
| 2 | Control | | 30.4 ± 2.6 |
| 3 | Group 1 | sample 3 (800) | 3.9 ± 0.5 |
| 4 | Group 2 | sample 3 (400) | 15.5 ± 4.6 |
| 5 | Group 3 | sample 3 (200) | 21.5 ± 4.0 |
| 6 | Group 4 | sample 4 (800) | 13.0 ± 2.9 |
| 7 | Group 5 | sample 1 (600) | 4.0 ± 0.8 |
| 8 | Group 6 | sample 2 (800) | 5.4 ± 0.7 |
| 9 | Group 7 | sample 1/sample 3 = 1/1 (400) | 9.3 ± 2.2 |
| 10 | Group 8 | sample 5 (600) | 7.6 ± 2.4 |
| 11 | Group 9 | reference sample 1 (800) | 27.3 ± 3.7 |

Test Example 2

Antiproliferative action of tumor and metastasis inhibition action of tumor were examined and evaluated by the following method about samples concerning the present invention. The Lewis lung cancer (it is abbreviated to LLC as follows) cell which was sold in lots from Institute of Physical and Chemical Research, was suspended to phosphoric acid/physiology salt buffer solution (pH 7.4). On the other hand, normal mice (7 mice/1 group) were used after breeding C57BL/6J female mice (6 week old, purchased from Kurea Japan, Inc.) preliminarily for one week. Under nembutal anesthesia the mice were exposed spleen through a small incision, and after injecting the LLC cell suspension (number of the LLC cell: $1.0 \times 10^5$) into the exposed spleen, the small incision was sewed up promptly. After 12 hours of LLC cell transplantation, the mice were orally administered agaricus mushroom extract (sample 1) 100 mg/kg (body weight) or 300 mg/kg (body weight) once a day for 20 days in succession. Distilled water was administered to a normal group and control group (LLC tumor-bearing mice) instead of sample 1. During this test period, the propagation degree of cancer cell was measured every two or three days by measuring quantity of carcinoma tissue volume (it was calculated with (major axis)×(minor axis)$^2$/2). On the 21st day after cancer cell transplantation, under ether anesthesia, mice of each group were taken venous blood sample into heparin tube, and white blood cell count, red blood cell count and hemoglobin dosage in the blood were measured by a call counter of blood cell. In addition, mice were slaughtered after collection of blood, and carcinoma tissue, liver, lung, spleen and thymus gland were removed and weighed, and then the number of cancer cell colony which spread to pulmonary tissue was measured under stereoscopic microscope.

Quantity of volume of tumor tissue in the LLC cell transplantation mice are shown in Table 3, weight of carcinoma tissue and each organ are shown in Table 4, and white blood cell count, red blood cell count, hemoglobin dosage and the number of transition colony to lung are shown in Table 5. Numerical values in each table are shown by average value±standard error. Fisher's Protect LSD Test was executed for significant difference assay, using a significant difference ($P<0.05$).

TABLE 3

| Group (n = 7) Material (mg/kg) | control | test group1 sample 1 (100) | test group2 sample 1 (300) |
|---|---|---|---|
| quantity of neoplasm volume (mm$^3$) after transplantation | | | |

TABLE 3-continued

| Group (n = 7) Material (mg/kg) | control | test group1 sample 1 (100) | test group2 sample 1 (300) |
|---|---|---|---|
| 5 days | 362 ± 33 | 290 ± 40 | 164 ± 30 (*) |
| 8 days | 461 ± 94 | 307 ± 64 | 247 ± 52 (*) |
| 10 days | 538 ± 108 | 322 ± 57 (*) | 301 ± 73 (*) |
| 14 days | 745 ± 142 | 493 ± 115 | 323 ± 101 (*) |
| 17 days | 872 ± 173 | 517 ± 121 (*) | 346 ± 108 (*) |
| 20 days | 1505 ± 362 | 608 ± 133 (*) | 410 ± 89 (*) |

(*): There was a significant difference in comparison with control group (P < 0.05)

TABLE 4

| Group (n = 7) Material (mg/kg) | normal | control | test group1 sample 1 (100) | test group2 sample 1 (300) |
|---|---|---|---|---|
| First body weight (g) | 17.9 ± 0.30 | 18.2 ± 0.21 | 18.0 ± 0.23 | 17.8 ± 0.25 |
| Last body weight (g) | 21.0 ± 0.41 | 19.9 ± 0.54 | 20.3 ± 0.72 | 20.0 ± 0.24 |
| Neoplasm weight (mg) | — | 1872 ± 604 | 531 ± 267* | 460 ± 115* |
| Spleen (g) | 0.07 ± 0.01* | 0.71 ± 0.03 | 0.35 ± 0.02* | 0.22 ± 0.02* |
| Liver (g) | 1.18 ± 0.05 | 1.28 ± 0.04 | 1.22 ± 0.03 | 1.24 ± 0.06 |
| Lung (mg) | 152.8 ± 4.51 | 166.8 ± 9.20 | 165.0 ± 6.76 | 155.0 ± 5.14 |
| Thymus gland (mg) | 47.0 ± 5.3 | 41.6 ± 10.3 | 45.2 ± 4.2 | 50.5 ± 3.0 |

*There was a significant difference in comparison with control group (P < 0.05)

TABLE 5

| Group (n = 7) Material (mg/kg) | normal | control | test group1 sample 1 (100) | test group2 sample 1 (300) |
|---|---|---|---|---|
| White blood cell count ($\times 10^3/\mu L$) | 3.65 ± 0.34 (*) | 4.85 ± 0.30 | 4.08 ± 0.54 (*) | 4.30 ± 0.79 (*) |
| Red blood cell count ($\times 10^4/\mu L$) | 782.0 ± 21.0 (*) | 494.2 ± 30.4 | 631.5 ± 26.2 (*) | 699.2 ± 51.5 (*) |
| Quantity of hemoglobin (g/100 mL) | 11.70 ± 1.09 | 6.93 ± 0.72 | 9.62 ± 0.43 (*) | 10.51 ± 0.54 (*) |
| Number of transition colony in lung | — | 21.5 ± 2.5 | 10.0 ± 1.5 | 7.0 ± 1.0 |

(*): There was a significant difference in comparison with control group (P < 0.05)

From data of table 3, it was showed that volume of neoplasm increased with time in control group (tumor-bearing mice) by transplantation of the LLC cell, and that increase of volume of neoplasm was inhibited in the group administered orally the test material (sample 1: agaricus mushroom extract including anhydrous glutamic acid) and the LLC cellular propagation was controlled.

From data of table 4, it was showed that increase of weight of neoplasm was inhibited clearly by intake of the test material, and that there was no significant difference in weight of each organ aside from spleen and final body weight between normal group, LLC cell transplantation group (control group) and test material administrated group.

Spleen weight increased in control group, but depression of increase was recognized in test material administrated group (there was significance difference with P<0.05). Therefore, it was proved that propagation of LLC cell was depressed by oral ingestion of test material (sample 1).

From data of table 5, it was showed that white blood cell count increased in control group compared with normal group, and that there was no significant difference between test material administrated group and normal group. Moreover, it was showed that red blood cell count and quantity of hemoglobin were significantly reduced and anemia state was shown in control group, but in test material administrated group, they were increased in significance (P<0.05) and anemia state recovered to close to normal by means of oral administration of agaricus fungus extract (sample 1). In addition, the number of transition colony of LLC cell in lung decreased in significance in test material administrated group compared with control group, and then it was proved that transition of cancer cell was inhibited by oral ingestion of the agaricus fungus extract which contained anhydrous glutamic acid (sample 1).

Test Example 3

Effect on immune function was examined and evaluated by the following method about samples concerning the present invention. Splenocyte was separated from spleen removed with test example 2. The splenocyte was layered on lymphocyte separate solution ("Lymphocyte Segregation Solution", made by Dainippon Pharmaceutical Co., Ltd.) and centrifuged for 30 minutes at 2000 rpm to separate lymphocyte. The coexisting erythrocyte was then hypotonic-solutionized and removed. The number of the lymphocyte was measured and adjusted to $1 \times 10^6$ cell count/100 µL. Antibody of various cell surface antigen ("CD 4, antimouse, FITC label", "CD 8, antimouse, FITC label" and "NK1.1, antimouse, R-PE label", made by Dainippon Pharmaceutical Co., Ltd.) 10 µL were added to the lymphocyte and reacted at 4 degrees Celsius for 30 minutes, after which it was washed twice in phosphate buffer (reagent for biochemical analysis made by Wako Pure Chemical Industries, LTD). The phosphate buffer was added there so that total volume was 1 mL, and then the numbers of CD 4$^+$, CD 8$^+$ and NK1.1$^+$ T cell were measured using a flow cytometry. The results are shown in Table 6.

TABLE 6

| Group (n = 7) Material (mg/kg) | normal | control | test group1 sample 1 (100) | test group2 sample 1 (300) |
|---|---|---|---|---|
| Number of the lymphocyte ($\times 10^7$/spleen) | (*) 3.68 ± 0.34 | 1.23 ± 0.20 | (*) 3.15 ± 0.41 | (*) 2.98 ± 0.90 |
| Number of CD4$^+$T CELL ($\times 10^6$/spleen) | (*) 6.0 ± 1.5 | 2.0 ± 0.5 | 3.5 ± 1.0 | (*) 5.5 ± 1.0 |
| Number of CD8$^+$T CELL ($\times 10^6$/spleen) | (*) 8.1 ± 1.0 | 3.5 ± 0.6 | 6.7 ± 0.7 | (*) 6.5 ± 1.0 |
| Number of NK1.1$^+$T CELL ($\times 10^5$/spleen) | 2.0 ± 0.5 | 2.0 ± 0.3 | (*) 4.5 ± 0.5 | (*) 3.5 ± 0.5 |

(*): There was a significant difference in comparison with control group (P < 0.05)

From data of table 6, it was showed that the number of the lymphocyte in spleen decreased in significance in control group (tumor-bearing mice) compared with normal group, and that this decrease was controlled in test material administrated group. In addition, it was proved that the numbers of CD 4$^+$ T cell and CD 8$^+$ T cell in spleen decreased in significance in control group (tumor-bearing mice) compared with normal group, and that decrease of the numbers of both cell was inhibited and the number of NK1.1$^+$ T cell was increased by intake of test material (sample 1). From these finding, it became clear that immune function was reinforced by oral ingestion of agaricus mushroom extract including anhydrous glutamic acid.

Example 6

Angiogenesis inhibition composition of the present invention comprising sample 1 and oolong tea leaf powder (3:2 (a weight ratio)) 5.0 kg, modified starch (a product made by Matsutani Chemical Industry Co, .Ltd, brand name: pine flow) 3.5 kg, tricalcium phosphate 0.3 kg, vitamin B$_1$ 0.3 kg, vitamin B$_2$ 0.2 kg, vitamin B$_6$ 0.2 kg, and vitamin C 0.5 kg were tucked into blender and mixed for 10 minutes. After the mixture was supplied into a tablet machine of the direct compression formulation type and made a tablet (diameter of 7 mm, height of 4 mm, 150 mg in weight), food in tablet form was produced experimentally by coating with shellac thin-film using coating machine. This tablet can be used for purpose of enhancement of internal immune strength, and prevention of lifestyle-related diseases such as diabetes mellitus or carcinoma.

Example 7

Butter 110 g, shortening 110 g, very-refined sugar 90 g and milk 100 mL were put in bowl for families, and one egg was more added there while whipping together. After mixing enough, a mixture of sample 2 and sample 3 (3:1, weight ratio) of the present invention 10 g was added there along with soft flour 190 g and baking powder 2 g, and then the mixture was kneaded enough together. After setting dough for 30 minutes, the mixed compound was split into 50 using mould and burnt in oven, and then a butter cookie was produced experimentally.

Example 8

Composition of the present invention comprising of sample 1, sample 2, and grape seed extract (made by Interhealthl company, brand name: Activin) (1:2:1 (a weight ratio)) 5 g were added to a commercial vegetable juice 1 L and mixed together, and then angiogenesis inhibition vegetable juice was produced experimentally for a person worried about malignant growth or rheumatoid arthritis. There was no inferiority in this in comparison with original vegetable juice at all.

Example 9

A mixture of sample 3/sample 5=1/1 (a weight ratio) 130 kg, propolis 90 kg, yellow beeswax 15 kg and corn oil 150 kg were mixed enough to become homogeneous liquid thing while warming to 40 degrees Celsius. This was supplied to the capsule filling up machine, and then gelatine covered-capsule formulation, of which quantity of one grain was 250 mg, was produced experimentally. This formulation can be used as edible composition (food and drink) or composition for medicine (drug) that oral ingestion is possible.

Example 10

Dry fruit body of an agaricus mushroom (*Agaricus blazei* Murill) was crushed. It was then added with chloroform/methanol=1/1 mixed solution after which the mixture was warmed to 50 degrees Celsius, and extract-processed for one hour to give a chloroform/methanol=1/1 extract. Methanol was added to the extract, and then methanol soluble layer was separated and collected except methanol insoluble materials including mannitol. Furthermore, hexane was added in the methanol soluble layer, and then hexane insoluble layer (sample 6) was collected. The hexane insoluble layer was then run through a silica gel column chromatography (silanised Silicagel 60 PF 254:Merck 7751, water/methanol=7/3), and ninhydrin reaction positive fractions (fraction No. 5 and 6) were collected. The fractions (fraction No. 5 and 6) were then run through HPLC (Shimadzu LC-8A system: Shimpak PREP-ODS (M), column: 20φ×250 mm, Shimadzu, RT, 6 ml/min, water/methanol=5/1), and ninhydrin reaction positive fractions (Rt=6 to 12 min) were collected. The fractions (Rt=6 to 12 min) were further run through HPLC (Shimadzu LC-8A system: Shimpak PREP-ODS (M), column: 20φ×250 mm, Shimadzu, RT, 6 ml/min, water), and ninhydrin reaction positive fraction (Rt=8 to 22 min) were collected. These ninhydrin reaction positive fractions were further refined by running through TLC (Silicagel 60 PF 254:Merck7747, water/methanol=1/100), and it was ensured that materials shown in the following were included.

More specifically, as a result of TLC (Silicagel 60, precoat TLC: Merck5715, water/methanol=1/100) assay, it was showed that there were alanine (the neighborhood of Rf (rate of flow)=0.27, ninhydrin positivity), proline (the neighborhood of Rf=0.20, ninhydrin positivity), gamma aminobutyric acid (the neighborhood of Rf=0.15, ninhydrin positivity) and unknown substance (the neighborhood of Rf=0.40, ninhydrin negativity) (49:5:25:21 (a weight ratio)). Subsequently, the unknown material was analyzed by NMR (nuclear magnetic resonance) spectrum analysis (device: Varian Unity Inova 500) and mass spectrum analysis (device: M-4000H, made by Hitachi, Ltd.), the results were 1H-NMR spectra (δ ppm, D$_2$O): 2.09, 2.39 (each 1H, m, H-3), 2.50 (2H, m, H-4), and 4.22 (1H, dd, J=5.2 and 9.0 Hz), 13C-NMR spectra (δ ppm, D$_2$O): 184 (COOH or —C═O—), 182 (—C═O—), 57 (—CH—), $\overline{32}$ (—O═C—CH$_2$—), and $\overline{28}$ (—CH$_2$—CH$_2$—), and mass spectrum $\overline{(m/z)}$: 42, 84 and 129 (M+). In addition, the result of Optical Rotatory Dispersion (ORD) spectrum analysis (made by JASCO Corporation (NIHON BUNKOU), ORD/UV-820) was [alpha]$_D^{23}$ −11.5° (c=2, H$_2$O). From these assay results, the unknown material was identified as L-pyroglutamic acid.

Example 11

By means of culture apparatus of 10 liters capacity, while aerating (2 vvm) and stirring (150 rpm), inoculum culture broth of *Phellinus linteus* (1 liter) was incubated in culture medium including glucose (5% by weight), yeast extract (0.5% by weight) and poly peptone (1.5% by weight) at 26 degrees Celsius for seven days, and culture mycelium (200 g) was collected. The culture mycelium was dried and crushed to give mycelium powder. A hexane/ethanol/water=3/4/1 mixed solvent was then added to the mycelium powder after which the mixture was warmed to 40 degrees Celsius, and extract-processed for 30 minutes to give an soluble material (sample 7). The soluble material was further fractionation-processed by ethanol, and an ethanol soluble layer was separated and collected. The ethanol soluble layer was then fractionation-processed by hexane, and hexane insoluble layer was collected. The hexane insoluble layer was fractionated and purified by silica gel column chromatography, HPLC, and TLC as same as example 10. Existence of L-pyroglutamic acid was ensured from results of mass spectrometry and nuclear magnetic resonance assay etc.

Example 12

L-pyroglutamic acid sodium was prepared in accordance with conventional method. More specifically, L-pyroglutamic acid aqueous solution (30% by weight) was added to a flask with stirrer, and while stirring slowly at room temperature, sodium hydroxide aqueous solution (0.5N) was added there untill no pH fluctuation. After salting out, the solution was dried to give L-pyroglutamic acid sodium (sample 8).

Example 13

DL-pyroglutamic acid sodium (sample 9) was prepared using the same way as in example 12 except that DL-glutamic acid substituted for L-glutamic acid of raw materials.

Example 14

Dry fruit body of *Agaricus blazei* Murill was crushed, and water was added there to extract-process using hot water at 80-95 degrees Celsius by conventional method. The extract was then dried under reduced pressure to prepare a hot water-extract of agaricus fungus. Ethanol multiplied by three (weight) was added to 40% by weight aqueous solution of the hot water-extract, and after mixing, ethanol layer was collected. The ethanol layer was then dried under reduced pressure to give ethanol soluble material. The ethanol soluble material was washed by hexane of 5 times (weight), and then dried under reduced pressure to prepare hexane insoluble material (sample 10).

Test Example 4

Angiogenesis inhibition action of pyroglutamic acid, its derivatives, and various processed materials containing them concerning the present invention was examined by degree of angiogenesis induced by means of MATRIGEL™ matrix (Becton Dikinson Labware company, following "MATRIGEL") according to the same method as test example 1.

More specifically, normal mice (5 mice/1 group) were used after breeding C57BL/6 female mice (5 week old, purchased from Charles River JAPAN, Inc.) preliminarily for one week. While cooling test materials as shown in the following, each of the test materials 0.5 ml were transplanted to subcutaneous of abdomen of the mice. MATRIGEL was taken out on the sixth day after transplantation, and state of angiogenesis was observed. In addition, the MATRIGEL was freeze-dried, and it was weighed. Furthermore, pure water 1 ml was added to the MATRIGEL. After homogenizing by Polytron and centrifuging at 2000 rpm for five minutes, supernatant was filtrated through filter with 0.2 μm and hemoglobin dosage was measured by using Hemoglobin-TestWako™ (product made in Wako Pure Chemical Industries, Ltd.).

Group 0 of nothing addition: MATRIGEL

Control group: MATRIGEL, heparin (64 units), Acidic Fibroblast Growth Factor (it is abbreviated to a-FGF as follows.) (1 ng/ml)

Group 1 of test material addition: MATRIGEL, heparin (64 units), a-FGF (1 ng/ml), sample 8 (800 μg/ml)

Group 2 of test material addition: MATRIGEL, heparin (64 units), a-FGF (1 ng/ml), sample 8 (400 μg/ml)

Group 3 of test material addition: MATRIGEL, heparin (64 units), a-FGF (1 ng/ml), sample 8 (200 μg/ml)

Group 4 of test material addition: MATRIGEL, heparin (64 units), a-FGF (1 ng/ml), sample 9 (800 μg/ml)

Group 5 of test material addition: MATRIGEL, heparin (64 units), a-FGF (1 ng/ml), sample 6 (600 μg/ml)

Group 6 of test material addition: MATRIGEL, heparin (64 units), a-FGF (1 ng/ml), sample 7 (800 μg/ml)

Group 7 of test material addition: MATRIGEL, heparin (64 unit), a-FGF (1 ng/ml), sample 6+sample 8 (for each 200 μg/ml)

Group 8 of test material addition: MATRIGEL, heparin (64 units), a-FGF (1 ng/ml), sample 10 (600 μg/ml)

Group 9 of test material addition: MATRIGEL, heparin (64 units), a-FGF (1 ng/ml), reference sample 1 (800 μg/ml)

A test result was shown in Table 7.

The numerical values of Table 7 were displayed in n=5, average value±standard error.

As is apparent from Table 7, in control group, angiogenesis was promoted remarkably and weight of MATRIGEL and hemoglobin dosage were increased compared with a group 0 of nothing addition.

On the other hand, in groups of test material addition, augmentation of weight of MATRIGEL and hemoglobin dosage was concentration-dependent controlled at the group using sample 8 (L-pyroglutamic acid salt), and these results showed excellent angiogenesis inhibition effect. The group using sample 9 (DL-pyroglutamic acid salt) was also recognized an effect, which is slightly low, but almost equal to sample 8, of angiogenesis inhibition. In addition, sample 6 (purification material of agaricus mushroom extract) and sample 7 (extract of *Phellinus linteus*) also showed strong angiogenesis inhibition effect. However, the angiogenesis inhibition effect was small with reference sample 1 (hot water extract of an agaricus mushroom). Furthermore, presence of angiogenesis inhibitory effect was also examined about alanine, proline and gamma aminobutyric acid similarly, but the angiogenesis inhibitory effect was not recognized in these materials.

TABLE 7

| Group n = 5 | material (µg/mL) | MATRIGEL weight (mg) | Quantity of hemoglobin (mg/MATRIGEL) |
|---|---|---|---|
| Group 0 (Normal) | | 100.0 ± 12.1 | 5.3 ± 1.7 |
| Control | | 393.6 ± 22.7 | 33.0 ± 3.4 |
| Group 1 | sample 8 (800) | 121.5 ± 28.1 | 4.8 ± 1.2 |
| Group 2 | sample 8 (400) | 190.2 ± 30.4 | 17.5 ± 3.6 |
| Group 3 | sample 8 (200) | 265.3 ± 18.6 | 23.4 ± 2.0 |
| Group 4 | sample 9 (800) | 209.0 ± 30.8 | 15.8 ± 2.7 |
| Group 5 | sample 6 (600) | 110.7 ± 10.3 | 4.0 ± 0.5 |
| Group 6 | sample 7 (800) | 136.4 ± 24.5 | 6.1 ± 2.4 |
| Group 7 | sample 6/sample 8 = 1/1 (400) | 150.5 ± 23.1 | 8.3 ± 1.8 |
| Group 8 | sample 10 (600) | 154.1 ± 27.2 | 9.0 ± 4.3 |
| Group 9 | reference sample 1 (800) | 320.4 ± 35.2 | 30.5 ± 4.5 |

MATRIGEL ™ (Becton Dikinson Labware company) matrix

Test Example 5

Antiproliferative action of tumor and metastasis control action of tumor were examined and evaluated according to the same method as Test example 2 except the following condition. 7 mice/1 group was replaced with 8 mice/1 group. Sample 1 was replaced with sample 6. The period of administration was 30 days instead of 20 days. The propagation degree of cancer cell was measured every 3 to 5 days instead of every 2 to 3 days. Slaughter of mice was conducted on the 31st day after cancer cell transplantation, instead of the 21st day.

Quantity of volume of tumor tissue in the LLC cell transplantation mice are shown in Table 8, weight of carcinoma tissue and each organ are shown in Table 9, and white blood cell count, red blood cell count, hemoglobin dosage and the number of transition colony to lung are shown in Table 10. Numerical values in each table are shown by average value±standard error. Fisher's Protect LSD Test was executed for significant difference assay, using a significant difference ($P<0.05$).

TABLE 8

| Group (n = 8) Material (mg/kg) | control | test group1 sample 6 (100) | test group2 sample 6 (300) |
|---|---|---|---|
| quantity of neoplasm volume (mm$^3$) after transplantation | | | |
| 7 days | 405 ± 40 | 285 ± 72 | 182 ± 31 (*) |
| 12 days | 617 ± 84 | 310 ± 94 (*) | 244 ± 83 (*) |
| 17 days | 806 ± 137 | 552 ± 108 | 317 ± 105 (*) |
| 21 days | 1430 ± 280 | 503 ± 131 (*) | 416 ± 122 (*) |
| 24 days | 1916 ± 325 | 745 ± 186 (*) | 503 ± 169 (*) |
| 30 days | 2190 ± 382 | 1067 ± 292 (*) | 670 ± 213 (*) |

(*): There was a significant difference in comparison with control group ($P < 0.05$)

TABLE 9

| Group (n = 8) Material (mg/kg) | normal | control | test group1 sample 6 (100) | test group2 sample 6 (300) |
|---|---|---|---|---|
| First body weight (g) | 18.5 ± 0.25 | 18.3 ± 0.34 | 18.5 ± 0.26 | 18.2 ± 0.22 |
| Last body weight (g) | 21.4 ± 0.36 | 23.1 ± 0.54 | 21.6 ± 0.87 | 22.1 ± 0.43 |
| Neoplasm weight (mg) | — | 3061 ± 785 | 745 ± 403 | 480 ± 130 |
| Spleen (g) | 0.08 ± 0.02* | 1.43 ± 0.07 | 0.81 ± 0.10* | 0.45 ± 0.03* |
| Liver (g) | 1.21 ± 0.05 | 1.39 ± 0.10 | 1.25 ± 0.05 | 1.22 ± 0.04 |
| Lung (mg) | 164.8 ± 7.1 | 187.7 ± 15.2 | 184.4 ± 13.1 | 175.0 ± 5.2 |
| Thymus gland (mg) | 58.5 ± 3.9 | 46.8 ± 6.6 | 47.9 ± 4.9 | 51.5 ± 5.0 |

(*): There was a significant difference in comparison with control group ($P < 0.05$)

TABLE 10

| Group (n = 8) Material (mg/kg) | normal | control | test group1 sample 6 (100) | test group2 sample 6 (300) |
|---|---|---|---|---|
| White blood cell count ($\times 10^3/\mu L$) | 3.32 ± 0.18 | (*1) 5.73 ± 1.40 | 4.72 ± 1.13 | 4.12 ± 0.59 |
| Red blood cell count ($\times 10^4/\mu L$) | (*) 799.0 ± 7.4 | 506.3 ± 78.4 | (*) 692.6 ± 37.2 | (*) 743.2 ± 22.0 |
| Quantity of hemoglobin (g/100 mL) | (*) 12.4 ± 0.09 | 7.80 ± 1.25 | (*) 10.6 ± 0.59 | (*) 11.3 ± 0.39 |
| Number of transition colony in lung | — | 30.0 ± 2.8 | (*) 15.8 ± 2.5 | (*) 13.6 ± 1.4 |

(*): There was a significant difference in comparison with control group ($P < 0.05$)
(*1): There was a significant difference in comparison with normal group ($P < 0.05$)

From data of table 8, it was showed that volume of neoplasm increased with time in control group (tumor-bearing mice) because of transplantation of the LLC cell, and that increase of volume of neoplasm was inhibited in the group administered orally the test material (sample 6: agaricus mushroom extract including pyroglutamic acid) and the LLC cellular propagation was controlled.

From data of table 9, it was showed that increase of weight of neoplasm was inhibited clearly by intake of the test material, and that there was no significant difference in weight of each organ aside from spleen and final body weight between normal group, LLC cell transplantation group (control group) and test material administrated group. Spleen weight increased in control group, but depression of increase was recognized in test material administrated group (there was significance difference with P<0.05). Therefore, it was proved that propagation of LLC cell was depressed by oral ingestion of test material (sample 6).

From data of table 10, it was showed that white blood cell count increased in significance in control group compared with normal group, and that there was no significant difference between test material administrated group and normal group. Moreover, it was showed that red blood cell count and quantity of hemoglobin were significantly reduced and anemia state was shown in control group, but in test material administrated group, they were increased in significance (P<0.05) and anemia state recovered to close to normal by means of oral administration of agaricus fungus extract (sample 6). In addition, the number of transition colony of LLC cell in lung decreased in significance in test material administrated group compared with control group, and then it was proved that transition of cancer cell was inhibited by oral ingestion of the agaricus fungus extract which contained pyroglutamic acid (sample 6).

Test Example 6

Effect on immune function was examined and evaluated by the following method about samples concerning the present invention. Splenocyte was separated from spleen removed with test example 5. The splenocyte was processed according to the same method as test example 3, and then the numbers of CD 4$^+$, CD 8$^+$ and NK1.1$^+$ T cell were measured using a flow cytometry. The results are shown in Table 11.

TABLE 11

| Group (n = 8) Material (mg/kg) | normal | control | test group1 sample 6 (100) | test group2 sample 6 (300) |
|---|---|---|---|---|
| Number of the lymphocyte (×10$^7$/spleen) | (*) 3.52 ± 0.48 | 1.47 ± 0.22 | (*) 2.84 ± 0.36 | (*) 3.01 ± 0.45 |
| Number of CD4$^+$T CELL (×10$^6$/spleen) | (*) 6.5 ± 0.8 | 2.1 ± 0.4 | 4.6 ± 0.5 | (*) 6.0 ± 1.1 |
| Number of CD8$^+$T CELL (×10$^6$/spleen) | (*) 7.7 ± 1.2 | 4.5 ± 0.7 | (*) 6.6 ± 0.6 | (*) 8.9 ± 0.8 |
| Number of NK1.1$^+$T CELL (×10$^5$/spleen) | (*) 1.7 ± 0.2 | 2.6 ± 0.3 | (*) 2.8 ± 0.3 | (*) 4.0 ± 0.5 |

(*): There was a significant difference in comparison with control group (P < 0.05)

From data of table 11, it was showed that the number of the lymphocyte in spleen decreased in significance in control group (tumor-bearing mice) compared with normal group, and that this decrease was controlled in test material administrated group. In addition, it was also proved that the numbers of CD 4$^+$ T cell and CD 8$^+$ T cell in spleen decreased in significance in control group (tumor-bearing mice) compared with normal group, and that decrease of the numbers of both cell was inhibited and the number of NK1.1$^+$ T cell was increased by intake of test material (sample 6). From these finding, it became clear that immune function was reinforced by oral ingestion of agaricus mushroom extract including anhydrous glutamic acid.

Example 15

Angiogenesis inhibition composition of the present invention comprising sample 10, oolong tea leaf powder, and Guava leaf hot water extract (3:2:1 (a weight ratio)) 10.0 kg, modified starch (made by Matsutani Chemical Industry Co, .Ltd, brand name: pine flow) 7.0 kg, tricalcium phosphate 0.5 kg, vitamin B$_1$ 0.4 kg, vitamin B$_2$ 0.4 kg, vitamin B$_6$ 0.5 kg, and vitamin C 1.2 kg were tucked into blender and mixed for 10 minutes. After the mixture was supplied into a tablet machine of the direct compression formulation type and made a tablet (diameter of 7 mm, a height of 4 mm, 150 mg in weight), food in tablet form was produced experimentally by coating with shellac thin-film using coating machine. This tablet can be used for purpose of enhancement of internal immune strength, and prevention of lifestyle-related diseases such as diabetes mellitus or carcinoma.

Example 16

Butter 120 g, shortening 100 g, very-refined sugar 100 g and milk 100 mL were put in bowl for families, and one egg was more added there while whipping together. After mixing enough, a mixture of sample 6, sample 7, and sample 8 (2:2:1, weight ratio) of the present invention 30 g was added there along with soft flour 200 g and baking powder 2 g, and then the mixture was kneaded enough together. After setting dough for 30 minutes, the mixed compound was split into 50 using mould and burnt in oven, and then butter cookies were produced experimentally.

Example 17

Composition of the present invention comprising of sample 8, sample 10, and grape seed extract (made by Interhealthl company, brand name: Activin) (1:2:1 (a weight ratio)) 20 g were added to a commercial vegetable juice 1 L and mixed together, and then angiogenesis inhibition vegetable juice was produced experimentally for use in antioxidation of tissue or prevention of diseases such as malignant, rheumatoid arthritis, and diabetes mellitus. There was no inferiority in this in comparison with original vegetable juice at all.

Example 18

A mixture of sample 6/sample 10=1/1 (a weight ratio) 100 kg, Ginkgo biloba extract 20 kg, shark cartilage extract 30 kg, yellow beeswax 10 kg and corn oil 140 kg were mixed enough to give homogeneous liquid thing while warming to 80 degrees Celsius. This was supplied to the capsule filling up machine, and then gelatine covered-capsule formulation, of which quantity of one grain was 250 mg, was produced experimentally. This formulation can be used as edible composition (food and drink) or composition for medicine (drug) that oral ingestion is possible.

This invention is not limited to the above embodiments and explanation thereof, and variations and modifications can be effected within the scope which does not depart from the description in the claims and can be easily conceived by a person having ordinary skill in the art.

What is claimed is:

1. A method for inhibiting angiogenesis, in connection with treating Lewis Lung Cancer Cells or rheumatoid arthritis, which comprises administering to a person or an animal in need thereof a composition selected from the group consisting of Formula (1) as an isolated compound or, a hydrochloride salt thereof, pyroglutamic acid, and sodium salt of pyroglutamic acid, including a pharmaceutically acceptable carrier or an edible carrier

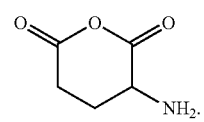

(1)

2. The method according to claim 1, wherein said compound of formula (1) and pyroglutamic acid are L-type or DL-type.

* * * * *